United States Patent [19]
Thenappan et al.

[11] Patent Number: 6,010,997
[45] Date of Patent: Jan. 4, 2000

[54] COMPOSITIONS OF 1-BROMOPROPANE, NITROMETHANE OR ACETONITRILE AND AN ALCOHOL

[75] Inventors: Alagappan Thenappan; Leonard Michael Stachura, both of Erie County; Martin Richard Paonessa, Niagara County; Kane David Cook, Erie County, all of N.Y.

[73] Assignee: Alliedsignal Inc., Morristown, N.J.

[21] Appl. No.: 09/104,796

[22] Filed: Jun. 25, 1998

[51] Int. Cl.$^7$ .............................. C11D 7/30; C11D 7/50; C23G 5/028

[52] U.S. Cl. .................. 510/410; 510/258; 510/264; 510/266; 510/273; 510/409; 510/411; 134/42; 134/40; 252/364

[58] Field of Search ..................... 510/409, 410, 510/411, 412, 258, 264, 266, 273; 570/111, 112, 118; 134/42, 40; 252/364

[56] References Cited

U.S. PATENT DOCUMENTS

| | | | |
|---|---|---|---|
| 3,564,061 | 2/1971 | Correia et al. | 570/110 |
| 3,723,331 | 3/1973 | Correia | 570/110 |
| 3,878,256 | 4/1975 | Richtzenhain et al. | 570/110 |
| 5,492,645 | 2/1996 | Oshima et al. | 252/171 |
| 5,665,170 | 9/1997 | Lee et al. | 134/19 |
| 5,665,172 | 9/1997 | Oshima et al. | 134/40 |
| 5,690,862 | 11/1997 | Moore, Jr. et al. | 252/364 |
| 5,792,277 | 8/1998 | Shubkin et al. | 134/19 |

FOREIGN PATENT DOCUMENTS

| | | |
|---|---|---|
| 3097793 | 4/1991 | Japan . |
| 3176433 | 7/1991 | Japan . |
| 5295159 | 11/1993 | Japan . |
| 6220494 | 8/1994 | Japan . |
| 8-67643 | 3/1996 | Japan . |
| 8067643 | 3/1996 | Japan . |
| 8311675 | 11/1996 | Japan . |
| 8337795 | 12/1996 | Japan . |
| WO 96/36688 | 11/1996 | WIPO . |
| WO 96/36689 | 11/1996 | WIPO . |
| WO 97/16583 | 5/1997 | WIPO . |
| WO 97/32001 | 9/1997 | WIPO . |
| WO 97/32964 | 9/1997 | WIPO . |

OTHER PUBLICATIONS

Chemical Abstracts 108:174370, Wisniak et al, "Vapor–liquid equilibrium at 760 mm Hg in the systems propyl bromide–tert–butyl alcohol and propyl bromide–p–xylene", 1988.

*Primary Examiner*—Christine Skane
*Attorney, Agent, or Firm*—Colleen D. Szuch; Marie Collazo

[57] ABSTRACT

The invention relates to novel compositions of 1-bromopropane, nitromethane or acetonitrile and at least one alcohol selected from the group consisting of ethanol, 2-propanol and 2-methyl-2-propanol and more particularly to azeotrope-like compositions based on these compounds which are useful as solvents in refrigeration flushing, oxygen system cleaning and vapor degreasing applications.

16 Claims, No Drawings

COMPOSITIONS OF 1-BROMOPROPANE, NITROMETHANE OR ACETONITRILE AND AN ALCOHOL

FIELD OF THE INVENTION

This invention relates to compositions of 1-bromopropane, nitromethane or acetonitrile and at least one alcohol and more particularly to azeotrope-like compositions based on these compounds. These mixtures are useful as solvents for use in refrigeration flushing, oxygen system cleaning, and vapor degreasing applications including electronics cleaning.

BACKGROUND OF THE INVENTION

1-Bromopropane based fluids have found widespread use in industry for solvent cleaning, i.e. vapor degreasing, cold cleaning and ultrasonic cleaning of complex metal parts, circuit boards, electronic components, implantable prosthetic devices, optical equipment and others.

In its simplest form, vapor degreasing or solvent cleaning consists of exposing a room temperature object to be cleaned to the vapors of a boiling solvent. Vapors condensing on the object provide clean distilled solvent to wash away grease or other contaminants. Final evaporation of the solvent from the object leaves no residue on the object.

For difficult to remove soils where elevated temperature is necessary to improve the cleaning action of the solvent, or for large volume assembly line operations where the cleaning of metal parts and assemblies must be done efficiently, a vapor degreaser is employed. The conventional operation of a vapor degreaser consists of immersing the part to be cleaned in a sump of boiling solvent which removes the bulk of the soil, thereafter immersing the part in a sump containing freshly distilled solvent near room temperature, and finally exposing the part to solvent vapors over the boiling sump which condense on the cleaned part. The part can also be sprayed with distilled solvent before final rinsing.

Azeotropic or azeotrope-like compositions are particularly desired because they do not fractionate upon boiling. This behavior is desirable because in the previously described vapor degreasing equipment in which these solvents are employed, redistilled material is generated for final rinse-cleaning. Thus, the vapor degreasing system acts as a still. Unless the solvent composition exhibits a constant boiling point, i.e., is azeotrope-like, fractionation will occur and undesirable solvent distribution may act to upset the cleaning and safety of processing.

The art is continually seeking new solvent mixtures which offer alternatives for the above-described applications. Currently, environmentally acceptable materials are of particular interest because the traditionally used fully halogenated chlorocarbons and chlorofluorocarbons have been implicated in causing environmental problems associated with the depletion of the earth's protective ozone layer. Mathematical models have substantiated that 1-bromopropane will not adversely affect atmospheric chemistry because its contribution to stratospheric ozone depletion and global warming in comparison to the fully halogenated chlorocarbons and chlorofluorocarbons species is negligible. The ozone depletion potential of 1-bromopropane is 0.002–0.03, which is significantly lower than the ozone depletion potentials of 1,1,2-trichloro-1,2,2-trifluoroethane or CFC-113 (0.8) and 1,1-dichloro-1-fluoroethane or HCFC-141 b (0.11). The global warming potential of 1-bromopropane (0.31) is also significantly lower than CFC-113 (5000) and HCFC-141b (630).

The art has also looked to compositions which include components which contribute additionally desired characteristics, such as polar functionality, increased solvency power, and stabilizers while retaining those properties exhibited by the prior art chlorofluorocarbons including chemical stability, low toxicity, and non-flammability.

It is accordingly an object of this invention to provide novel ternary compositions based on 1-bromopropane, nitromethane or acetonitrile and at least one alcohol, and preferably azeotrope-like compositions, which are useful in solvent and other applications and which meet the above criteria.

The present compositions are advantageous for the following reasons. The 1-bromopropane component has an ozone depletion potential of 0.002–0.03 and has reasonable solvency characteristics. The alcohol has good solvent properties to enable the cleaning and dissolution of ionics, flux resin and oils. The nitromethane or acetonitrile component is known to inhibit the decomposition of 1-bromopropane. Thus, when these components are combined in effective amounts, an efficient, stable, environmentally acceptable solvent composition results.

DESCRIPTION OF THE INVENTION

The invention relates to novel compositions comprising effective amounts of 1-bromopropane, nitromethane or acetonitrile, and at least one alcohol selected from the group consisting of ethanol, 2-propanol and 2-methyl-2-propanol. The invention further relates to azeotrope-like compositions comprising from about 65 to about 99 weight percent 1-bromopropane; from about 1 to about 35 weight percent nitromethane or acetonitrile; and, based on the total weight of said 1-bromopropane and nitromethane or acetonitrile, from about 1 to about 35 weight percent of at least one alcohol selected from the group consisting of ethanol, 2-propanol and 2-methyl-2-propanol, which compositions boil at from about 60.2° C. to about 67.5° C.±about 2.0° C. at 760 mmHg.

The 1-bromopropane, nitromethane, acetonitrile and alcohol components of the invention are commercially available in pure form and may be obtained readily.

The term "azeotrope-like" is used herein for the preferred mixtures of the invention because in the claimed proportions, the compositions of 1-bromopropane, nitromethane or acetonitrile and at least one alcohol are constant boiling or essentially constant boiling. All compositions within the indicated ranges, as well as certain compositions outside the indicated ranges, are azeotrope-like, as defined more particularly below.

From fundamental principles, the thermodynamic state of a fluid is defined by four variables: pressure, temperature, liquid composition, and vapor composition, or P-T-X-Y, respectively. An azeotrope is a unique characteristic of a system of two or more components where X and Y are equal at a stated P and T. In practice, this means that the components cannot be separated during a phase change, and therefore are useful in solvent and aerosol solvent applications.

For the purposes of this discussion, by azeotrope-like composition is intended to mean that the composition behaves like a true azeotrope in terms of its constant boiling characteristics or tendency not to fractionate upon boiling or evaporation. Thus, in such systems, the composition of the vapor formed during evaporation is identical or substantially identical to the original liquid composition. Hence during boiling or evaporation the liquid composition changes, if at all, only slightly. This is contrasted with non-azeotrope-like compositions in which the liquid and vapor compositions change substantially during evaporation or condensation.

One way to determine whether a candidate mixture is azeotrope-like within the meaning of this invention, is to distill a sample thereof under conditions (i.e., resolution—number of plates) which would be expected to separate the mixture into its separate components. If the mixture is not an azeotrope or azeotrope-like, the mixture will fractionate, i.e., separate into its various components with the lowest boiling component distilling off first, and so on. If the mixture is azeotrope-like, some finite amount of the first distillation cut will be obtained which contains all of the mixture components and which is constant boiling or behaves as a single substance. This phenomenon cannot occur if the mixture is not azeotrope-like, i.e., if it is not part of an azeotrope system.

It follows from the above that another characteristic of azeotrope-like compositions is that there is a range of compositions containing the same components in varying proportions which are azeotrope-like. All such compositions are intended to be covered by the term azeotrope-like as used herein. As an example, it is well known that at different pressures the composition of a given azeotrope will vary at least slightly as does the boiling point of the composition. Thus, an azeotrope of A and B represents a unique type of relationship but with a variable composition depending on the temperature and/or pressure. As is readily understood by persons skilled in the art, the boiling point of an azeotrope will vary with the pressure.

In the process embodiment of the invention, the compositions of the invention may be used to clean solid surfaces by treating said surfaces with said compositions in any manner well known in the art such as by dipping or use of open or closed vapor degreasing apparatus.

It should be understood that the present compositions may include one or more additional components (such as stabilizers, inhibitors or antioxidants), some of which may form new azeotrope-like compositions. Such additional components typically are added at the expense of 1-bromopropane and in amounts known to one skilled in the art. Preferably, such components are added in an amount of up to about 5 weight percent based on the weight of the 1-bromopropane component, and more preferably in an amount of up to about 5 weight percent based on the total weight of the composition. Any such compositions are considered to be within the scope of the present invention as long as the compositions contain all of the essential components described herein.

Stabilizers typically are added to solvent compositions to inhibit decomposition of the compositions; react with undesirable decomposition products of the compositions; and/or prevent corrosion of metal surfaces. Any combination of conventional stabilizers known to be useful in stabilizing halogenated hydrocarbon solvents may be used in the present invention. Suitable stabilizers include alkanols having 4 to 7 carbon atoms, nitroalkanes having 1 to 3 carbon atoms, 1,2-epoxyalkanes having 2 to 7 carbon atoms, phosphite esters having 12 to 30 carbon atoms, ethers having 3 or 4 carbon atoms, unsaturated compounds having 4 to 6 carbon atoms, acetals having 4 to 7 carbon atoms, ketones having 3 to 5 carbon atoms, and amines having 6 to 8 carbon atoms. Other suitable stabilizers will readily occur to those skilled in the art. See, for example, U.S. Pat. No. 5,665,172.

The present invention is more fully illustrated by the following non-limiting Examples.

EXAMPLES

The range over which the following compositions exhibit constant boiling behavior was determined using ebulliometry and then confirmed by distillation.

The ebulliometer used in this experiment consisted of a heated sump. The upper part of the ebulliometer connected to the sump was cooled thereby acting as a condenser for the boiling vapors, allowing the system to operate at total reflux. Measured quantities of the lower boiling material was charged into the ebulliometer and brought to a boil. Then, in separate identical experiments, measured amounts of the relevant high boiling component was titrated into the ebulliometer. The change in boiling point was measured with a platinum resistance thermometer.

A 5-plate Oldershaw distillation column with a cold water condensed automatic liquid dividing head was used to confirm the composition of the azeotrope-like compositions. The distillation column was charged with 1-bromopropane, nitromethane or acetonitrile and an alcohol and the composition was heated under total reflux for about an hour to ensure equilibration. A reflux ratio of 5:1 was employed. Approximately 50 percent of the original charges were collected in four similar-sized overhead fractions. The compositions of these fractions were analyzed using Gas Chromatography and are reported in the tables below.

The preferred and more preferred embodiments for each azeotrope-like composition of the invention are listed in the following tables. The proportions/ranges listed are understood to be prefaced by "about".

TABLE I

Preferred Compositions

| A (wt.%) | B (wt.%) | C (wt. % based on total weight A + B) | Boiling Point (° C. at 760 mmHg) |
|---|---|---|---|
| 89–99% 1-Bromopropane | 1–11% Nitromethane | 1–10% 2-Methyl-2-Propanol | 67.5 ± 2.0 |
| 89–99% 1-Bromopropane | 1–11% Nitromethane | 5–25% 2-Propanol | 64.9 ± 2.0 |
| 65–92% 1-Bromopropane | 8–35% Acetonitrile | 1–35% 2-Methyl-2-Propanol | 64.1 ± 2.0 |
| 65–92% 1-Bromopropane | 8–35% Acetonitrile | 5–30% Ethanol | 60.2 ± 2.0 |

TABLE II

More Preferred Compositions

| A (wt.%) | B (wt.%) | C (wt. % based on total weight A + B) | Boiling Point (° C. at 760 mmHg) |
|---|---|---|---|
| 92–99% 1-Bromopropane | 1–8% Nitromethane | 1–7% 2-Methyl-2-Propanol | 67.5 ± 1.0 |
| 92–99% 1-Bromopropane | 1–8% Nitromethane | 7–20% 2-Propanol | 64.9 ± 1.0 |
| 75–90% 1-Bromopropane | 10–25% Acetonitrile | 4–32% 2-Methyl-2-Propanol | 64.1 ± 1.0 |
| 75–90% 1-Bromopropane | 10–25% Acetonitrile | 10–30% Ethanol | 60.2 ± 1.0 |

TABLE III

Most Preferred Compositions

| A (wt.%) | B (wt.%) | C (wt. % based on total weight A + B) | Boiling Point (° C. at 760 mmHg) |
|---|---|---|---|
| 99% 1-Bromopropane | 1% Nitromethane | 3% 2-Methyl-2-Propanol | 67.5 ± 0.5 |
| 95% 1-Bromopropane | 5% Nitromethane | 10–15% 2-Propanol | 64.9 ± 0.5 |
| 82% 1-Bromopropane | 18% Acetonitrile | 6–30% 2-Methyl-2-Propanol | 64.1 ± 0.5 |
| 82% 1-Bromopropane | 18% Acetonitrile | 15–21% Ethanol | 60.2 ± 0.5 |

What is claimed:

1. Azeotrope-like compositions consisting essentially of from about 89 to about 99 weight percent 1-bromopropane; from about 1 to about 11 weight percent nitromethane; and, based on the total weight of said 1-bromopropane and nitromethane, from about 1 to about 10 weight percent 2-methyl-2-propanol wherein said compositions boil at 67.5° C.±2.0° C. at 760 mmHg.

2. Azeotrope-like compositions of claim 1 consisting essentially of from about 92 to about 99 weight percent 1-bromopropane; from about 1 to about 8 weight percent nitromethane; and, based on the total weight of said 1-bromopropane and nitromethane, from about 1 to about 7 weight percent 2-methyl-2-propanol wherein said compositions boil at 67.5° C.±1.0° C. at 760 mmHg.

3. The azeotrope-like compositions of claim 1 consisting essentially of about 99 weight percent 1-bromopropane; about 1 weight percent nitromethane; and, based on the total weight of said 1-bromopropane and nitromethane, about 3 weight percent 2-methyl-2-propanol wherein said compositions boil at 67.5° C.±0.5° C. at 760 mmHg.

4. A method for cleaning a surface of a substrate which comprises treating said surface with a composition of claim 1 in an amount effective to accomplish said cleaning.

5. Azeotrope-like compositions consisting essentially of from about 89 to about 99 weight percent 1-bromopropane; from about 1 to about 11 weight percent nitromethane; and, based on the total weight of said 1-bromopropane and nitromethane, from about 5 to about 25 weight percent 2-propanol wherein said compositions boil at about 64.9° C.±about 2.0° C. at 760 mmHg.

6. The azeotrope-like compositions of claim 5 consisting essentially of from about 92 to about 99 weight percent 1-bromopropane; from about 1 to about 8 weight percent nitromethane; and, based on the total weight of said 1-bromopropane and nitromethane, from about 7 to about 20 weight percent 2-propanol wherein said compositions boil at about 64.9° C.±about 1.0° C. at 760 mmHg.

7. The azeotrope-like compositions of claim 5 consisting essentially of about 95 weight percent 1-bromopropane; about 5 weight percent nitromethane; and, based on the total weight of said 1-bromopropane and nitromethane, from about 10 to about 15 weight percent 2-propanol wherein said compositions boil at about 64.9° C.±about 0.5° C. at 760 mmHg.

8. A method for cleaning a surface of a substrate which comprises treating said surface with a composition of claim 5 in an amount effective to accomplish said cleaning.

9. Azeotrope-like compositions consisting essentially of from about 65 to about 92 weight percent 1-bromopropane; from about 8 to about 35 weight percent acetonitrile; and, based on the total weight of said 1-bromopropane and acetonitrile, from about 1 to about 35 weight percent 2-methyl-2-propanol wherein said compositions boil at about 64.1° C.±about 2.0° C. at 760 mmHg.

10. The azeotrope-like compositions of claim 9 consisting essentially of from about 75 to about 90 weight percent 1-bromopropane; from about 10 to about 25 weight percent acetonitrile; and, based on the total weight of said 1-bromopropane and acetonitrile, from about 4 to about 32 weight percent 2-methyl-2-propanol wherein said compositions boil at 64.1° C.±about 1.0° C. at 760 mmHg.

11. The azeotrope-like compositions of claim 9 consisting essentially of about 82 weight percent 1-bromopropane; about 18 weight percent acetonitrile; and, based on the total weight of said 1-bromopropane and acetonitrile, from about 6 to about 30 weight percent 2-methyl-2-propanol wherein said compositions boil at about 64.1° C.±about 0.5° C. at 760 mmHg.

12. A method for cleaning a surface of a substrate which comprises treating said surface with a composition of claim 9 in an amount effective to accomplish said cleaning.

13. Azeotrope-like compositions consisting essentially of from about 65 to about 92 weight percent 1-bromopropane; from about 8 to about 35 weight percent acetonitrile; and, based on the total weight of said 1-bromopropane and acetonitrile, from about 5 to about 30 weight percent ethanol wherein said compositions boil at about 60.2° C.±about 2.0° C. at 760 mmHg.

14. The azeotrope-like compositions of claim 13 consisting essentially of from about 75 to about 90 weight percent 1-bromopropane; from about 10 to about 25 weight percent acetonitrile; and, based on the total weight of said 1-bromopropane and acetonitrile, from about 10 to about 25 weight percent ethanol wherein said compositions boil at about 60.2° C.±about 1.0° C. at 760 mmHg.

15. The azeotrope-like compositions of claim 13 consisting essentially of about 82 weight percent 1-bromopropane; about 18 weight percent acetonitrile; and, based on the total weight of said 1-bromopropane and acetonitrile, from about 15 to about 21 weight percent ethanol wherein said compositions boil at about 60.2° C.±about 0.5° C. at 760 mmHg.

16. A method for cleaning a surface of a substrate which comprises treating said surface with a composition of claim 13 in an amount effective to accomplish said cleaning.

* * * * *